(12) United States Patent
Girdhar

(10) Patent No.: US 10,335,511 B2
(45) Date of Patent: *Jul. 2, 2019

(54) BIOADHESIVE FOR OCCLUDING VESSELS

(71) Applicant: Covidien LP, Mansfield, MA (US)

(72) Inventor: Gaurav Girdhar, Ladera Ranch, CA (US)

(73) Assignee: Covidien LP, Mansfield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/597,470

(22) Filed: May 17, 2017

(65) Prior Publication Data

US 2017/0246340 A1    Aug. 31, 2017

Related U.S. Application Data

(60) Continuation of application No. 15/048,479, filed on Feb. 19, 2016, now Pat. No. 9,827,348, which is a division of application No. 14/502,413, filed on Sep. 30, 2014, now Pat. No. 9,295,752.

(51) Int. Cl.
   *A61L 24/04*   (2006.01)
   *A61L 24/10*   (2006.01)

(52) U.S. Cl.
   CPC .......... *A61L 24/108* (2013.01); *A61L 24/043* (2013.01); *A61L 2400/06* (2013.01)

(58) Field of Classification Search
   None
   See application file for complete search history.

(56) References Cited

U.S. PATENT DOCUMENTS

| | | | |
|---|---|---|---|
| 6,152,943 A | 11/2000 | Sawhney | |
| 6,371,975 B2 | 4/2002 | Cruise et al. | |
| 6,458,147 B1 | 10/2002 | Cruise et al. | |
| 6,562,059 B2 | 5/2003 | Edwards et al. | |
| 6,733,515 B1 | 5/2004 | Edwards et al. | |
| 6,743,248 B2 | 6/2004 | Edwards et al. | |
| 6,830,756 B2 | 12/2004 | Hnojewyj | |
| 6,887,974 B2 | 5/2005 | Pathak | |
| 6,899,889 B1 | 5/2005 | Hnojewyj et al. | |
| 6,949,114 B2 | 9/2005 | Milo et al. | |
| 6,994,686 B2 | 2/2006 | Cruise et al. | |
| 7,057,019 B2 | 6/2006 | Pathak | |
| 7,081,125 B2 | 7/2006 | Edwards et al. | |
| 7,220,270 B2 | 5/2007 | Sawhney et al. | |
| 7,247,314 B2 | 7/2007 | Hnojewyj et al. | |
| 7,279,001 B2 | 10/2007 | Addis et al. | |
| 7,318,933 B2 | 1/2008 | Hnojewyj | |
| 7,351,249 B2 | 4/2008 | Hnojewyj et al. | |
| 7,914,541 B2 | 3/2011 | Sawhney et al. | |
| 8,034,367 B2 | 10/2011 | Hnojewyj | |
| 8,383,144 B2 | 2/2013 | Hnojewyj | |
| 8,410,189 B2 | 4/2013 | Carnahan et al. | |
| 8,481,695 B2 | 7/2013 | Melvik et al. | |
| 8,535,709 B2 | 9/2013 | Kennedy et al. | |
| 9,295,752 B1* | 3/2016 | Girdhar | A61L 24/108 |
| 9,827,348 B2* | 11/2017 | Girdhar | A61L 24/108 |
| 2001/0018598 A1 | 8/2001 | Cruise et al. | |
| 2006/0040894 A1 | 2/2006 | Hunter et al. | |
| 2006/0045900 A1 | 3/2006 | Richard et al. | |
| 2007/0032451 A1 | 2/2007 | Thacker et al. | |
| 2007/0128152 A1 | 6/2007 | Hadba | |
| 2008/0293910 A1 | 11/2008 | Kaplamba | |
| 2010/0137241 A1 | 6/2010 | Elisseeff | |
| 2011/0033540 A1 | 2/2011 | Daniloff et al. | |

OTHER PUBLICATIONS

Ogsten et al. "Effects of Hyaluronic Acid Upon Diffusion of Solutes and Flow of Solvent," J. Physiol. (1961), 156, pp. 67-74.
Sandgren et al. "The diameter of the common femoral artery in healthy human: Influence of sex, age, and body size," J. Vascular Surgery, 1999, 29(3), 503-10.
Spector et al. "Optimizing Safe Femoral Access During Cardiac Catheterization" Catheterization and Cardiovascular Interventions 53:209-212 (2001).
Calbiochem, "Buffers—A Guide for the preparation and use of buffers in biological systems," 2006.
Sargeant et al., "An in situ forming collagen—PEG hydrogel for tissue regeneration," Acta Biomaterialia 8 (2002) 124-132.
Necas et al., "Hyaluronic acid (hyaluronan): a review" Veterinami Medicina, 53, 2008 (8): 397-411.
Steinberg, "Mucopolysaccharides for cosmetics," Cosmetic Technology, Feb. 1982, pp. 41-44.
Peng et al., "Experimental Optimization of an In Situ Forming Hydrogel for Hemmorrhage Control," 2008 Journal of Applied Biomedical Materials Research Part B: Applied Biomaterials, pp. 199-209.
Bakar et al., "Evaluation of the Neurotoxicity of the Polyethylene Glycol Hydrogel Dural Sealant," Turkish Neurosurgery, 2013, vol. 23, No. 1, pp. 16-24.
Mastropietro et al., "Rheology in Pharmaceutical Formulations—A Perspective," Journal of Developing Drugs, 2013, vol. 2, Issue 2, 6 pages.
Falcone et al., "Rheological and cohesive properties of hyaluronic acid," J Biomed Mater Res 76A: 721-728 (2006).

\* cited by examiner

*Primary Examiner* — Christina Bradley

(57) ABSTRACT

Bioadhesives and crosslinked gels therefrom are disclosed. The bioadhesives can be applied to a vessel for occluding the vessel. The present disclosure also describes kits that comprise the various components for preparing and applying the bioadhesives. Bioadhesives of the present disclosure include: (i) a biopolymer having one or more first chemically reactive amine groups; (ii) a biocompatible crosslinker having at least two second chemically reactive groups that can chemically react with the one or more first chemically reactive amine groups of the biopolymer; and (iii) a biocompatible rheological modifier.

26 Claims, 4 Drawing Sheets

BIOADHESIVE FOR OCCLUDING VESSELS

RELATED APPLICATIONS

This application is a Continuation of and claims the benefit of U.S. patent application Ser. No. 15/048,479 filed Feb. 19, 2016, which is a Division of and claims the benefit of U.S. patent application Ser. No. 14/502,413 filed Sep. 30, 2014, now U.S. Pat. No. 9,295,752, the disclosure of which is herein incorporated by reference in its entirety.

TECHNICAL FIELD

The present disclosure relates to a bioadhesive and cross-linked gels therefrom and to making and using the bioadhesive for occluding vessels.

BACKGROUND

Bioadhesives can be used to seal blood vessels. However, fluid at the site of application, such as blood, may prevent the bioadhesive from working properly. For example, in a vessel, blood may dilute the bioadhesive or wash it away entirely before the bioadhesive has an opportunity to adhere and/or crosslink.

One place it may be useful to use bioadhesives is within vessels, such as blood vessels. For example, spider veins (telangiectasias) are caused when small, superficial blood vessels dilate and rise above the skin surface, appearing most commonly on the face and legs. They can be red, purple or bluish in color, and can appear in noticeable small patches or can cover large areas of skin.

Telangiectasia develops in the legs often due to the presence of venous hypertension within underlying varicose veins or underlying venous reflux disease. Flow abnormalities within the medium sized veins of the leg (reticular veins) can also lead to the development of telangiectasia.

Current treatments for such modalities include the use of commercial sclerosants, e.g., sodium tetradecyl sulfate (STS) and polidocanol, which are injected into the vein and work by damaging the cell lining of blood vessels, causing them to close and eventually be replaced by other types of tissue. Such current treatment can require multiple sessions, and in some case can result in long term staining.

Biomaterial based treatments are also being proposed (but not approved for use) for spider vein treatment. The limitations of biomaterials are uncontrolled degradation of the biomaterial, weak adhesion, and insufficient or slow absorption of the vein into surrounding tissue. Some of these limitations may be caused by blood flowing through the vessel, thereby diluting or washing the biomaterial away before the biomaterial has an opportunity to properly cure. Further, biomaterial based treatments can also suffer from poor cosmetic effects (such as inflammation and necrosis and staining). Accordingly, a need exists for improved formulations that can occlude vessels in a mammal.

SUMMARY OF THE DISCLOSURE

An advantage of the present disclosure is a bioadhesive that can be readily used to occlude vessels, e.g., blood vessels of a mammal. The bioadhesive of the present disclosure may be implemented to realize one or more of the following advantages. The bioadhesive of the present disclosure has viscosity sufficient to displace fluids in a vessel, such as blood, while the bioadhesive crosslinks, but is still capable of being injected through a thin gauge needle. The bioadhesive crosslinks in place while preventing fluids, such as blood, from pushing back into the treatment area and washing the bioadhesive away before the bioadhesive has an opportunity to crosslink. Further, once crosslinked, the gel formed from the bioadhesive can have a color that cannot be seen through the skin, and can have a tactile feel similar to the vessel into which the bioadhesive was injected, thereby providing an immediate cosmetic and physiological effect.

These and other advantages are satisfied, at least in part, by a bioadhesive comprising: (i) a biopolymer having one or more first chemically reactive amine groups; (ii) a biocompatible crosslinker having at least two second chemically reactive groups that can chemically react with the one or more first chemically reactive amine groups; and (iii) a biocompatible rheological modifier.

Embodiments include one or more of the following features individually or combined. For example, the biopolymer can be a protein or a polysaccharide having one or more primary amines as the first chemically reactive groups. In other embodiments, the biopolymer is albumin. In some embodiments, the protein is collagen and the polysaccharide is a chitosan having one or more first chemically reactive amine groups. In other embodiments, the biopolymer is a synthetic polymer selected from the group consisting of amine functionalized polyethylene glycols, polyallylamine, and branched polyethylenimine. In some embodiments, the biocompatible crosslinker is a multi-arm polyethylene glycol (PEG) having at least two or more N-hydroxysuccinimide (NHS) ester groups as the second chemically reactive groups. In still further embodiments, the biocompatible rheological modifier can be a shear thinning fluid with a non-sheared viscosity between 0.5 Pa·s and 200 Pa·s. In some embodiments, the biocompatible rheological modifier is hyaluronic acid or a salt thereof, such as sodium hyaluronate. In other embodiments, the biopolymer is albumin having one or more primary amines as the first chemically reactive amine groups, the biocompatible crosslinker is a multi-arm PEG having at least two or more N-hydroxysuccinimide ester groups as the second chemically reactive groups and the biocompatible rheological modifier is sodium hyaluronate. In various embodiments, the concentration of the biopolymer in the bioadhesive is between 7.5 wt % to 5 wt %, and the bioadhesive has a pH of less than 7.4.

In accordance with the present disclosure, a bioadhesive can comprise: (i) a biopolymer having one or more first chemically reactive amine groups; (ii) a biocompatible crosslinker having at least two second chemically reactive groups that can chemically react with the one or more first chemically reactive amine groups; and (iii) a biocompatible rheological modifier, wherein the concentration of the biopolymer in the bioadhesive is less than 15% by weight.

Embodiments include one or more of the following features individually or combined. For example, the biopolymer can be a protein or a polysaccharide having one or more primary amines as the first chemically reactive amine groups. The biocompatible crosslinker can be a multi-arm PEG having at least two or more N-hydroxysuccinimide (NHS) ester groups as the second chemically reactive groups, for example. In other embodiments, the biopolymer is an albumin having one or more primary amines as the first chemically reactive amine groups, the biocompatible crosslinker is a multi-arm PEG having at least two or more N-hydroxysuccinimide ester groups as the second chemically reactive groups and the biocompatible rheological modifier is sodium hyaluronate.

In accordance with the present disclosure, a bioadhesive can comprise: (i) a biopolymer having one or more first chemically reactive amine groups; (ii) a biocompatible crosslinker having at least two second chemically reactive groups that can chemically react with the one or more first chemically reactive amine groups; and (iii) a biocompatible rheological modifier, wherein the bioadhesive has a gelation time of more than 5 minutes.

Embodiments include one or more of the following features individually or combined. For example, the biopolymer can be a protein or a polysaccharide having one or more primary amines as the first chemically reactive amine groups. In various embodiments, the biocompatible crosslinker is a multi-arm PEG having at least two or more N-hydroxysuccinimide (NHS) ester groups as the second chemically reactive groups. In still further embodiments, the biopolymer is an albumin having one or more primary amines as the first chemically reactive amine groups, the biocompatible crosslinker is a multi-arm PEG having at least two or more N-hydroxysuccinimide ester groups as the second chemically reactive groups and the biocompatible rheological modifier is sodium hyaluronate.

Another aspect of the present disclosure includes a method of preparing a bioadhesive and the gel therefrom. The method comprises: combining (i) a biopolymer having one or more first chemically reactive amine groups; (ii) a biocompatible crosslinker having at least two second chemically reactive groups that can chemically react with the one or more first chemically reactive amine groups; and (iii) a biocompatible rheological modifier, to form a bioadhesive. Advantageously, the biopolymer crosslinks with the biocompatible crosslinker to form a bioadhesive gel.

Embodiments include one or more of the following features individually or combined. For example, the method can include transferring the bioadhesive to a syringe suitable for injecting the bioadhesive into a vessel of a mammal. In some embodiments, the bioadhesive has a gelation time of more than 5 minutes. In some embodiments, the biopolymer is albumin. In other embodiments, the biopolymer is chitosan or the biopolymer is a synthetic polymer selected from the group consisting of amine functionalized polyethylene glycols, and branched polyethylenimine. In still further embodiments, the biocompatible crosslinker is a multi-arm PEG having at least two or more N-hydroxysuccinimide (NHS) ester groups as the second chemically reactive groups. In some embodiments, the biocompatible rheological modifier can be a shear thinning fluid with a non-sheared viscosity between 0.5 Pa·s and 200 Pa·s. In various embodiments, the biocompatible rheological modifier is hyaluronic acid or a salt thereof, such as sodium hyaluronate. In still further embodiments, the biopolymer is an albumin having one or more primary amines as the first chemically reactive amine groups, the biocompatible crosslinker is a multi-arm PEG having at least two or more N-hydroxysuccinimide ester groups as the second chemically reactive groups, and the biocompatible rheological modifier is sodium hyaluronate. Additional embodiments include mixing the biopolymer and the biocompatible rheological modifier in a first container; mixing the biocompatible crosslinker in a buffer solution in a second container; and mixing the contents of the first container and the second container together to form the bioadhesive, and wherein the buffer solution has a pH between 4.5 and 7.4.

In accordance with the present disclosure, a method of preparing a bioadhesive and gel therefrom includes combining (i) a formulation including a biopolymer having one or more first chemically reactive amine groups and a biocompatible rheological modifier with (ii) a formulation including a biocompatible crosslinker having at least two second chemically reactive groups that can chemically react with the one or more first chemically reactive amine groups, to form a bioadhesive wherein the biopolymer crosslinks with the biocompatible crosslinker to form a bioadhesive gel.

Embodiments include one or more of the following features individually or combined. For example, the biopolymer can be albumin. In some embodiments, the biocompatible crosslinker is a multi-arm PEG having at least two or more N-hydroxysuccinimide (NHS) ester groups as the second chemically reactive groups. In some embodiments, the biocompatible rheological modifier is hyaluronic acid or a salt thereof.

In accordance with the present disclosure, a method of preparing a bioadhesive and gel therefrom includes combining (i) a formulation including a biopolymer having one or more first chemically reactive amine groups and a biocompatible rheological modifier with (ii) a formulation including a buffer and a biocompatible crosslinker having at least two second chemically reactive groups that can chemically react with the one or more first chemically reactive amine groups, to form a bioadhesive wherein the biopolymer crosslinks with the biocompatible crosslinker to form a bioadhesive gel.

Embodiments include one or more of the following features individually or combined. For example, the biopolymer can be albumin. In some embodiments, the biocompatible crosslinker is a multi-arm PEG having at least two or more N-hydroxysuccinimide (NHS) ester groups as the second chemically reactive groups. In some embodiments, the biocompatible rheological modifier is hyaluronic acid or a salt thereof. In still further embodiments, the buffer has a pH between 4.5 and 7.4. Additional embodiments further include the biocompatible rheological modifier is a shear thinning fluid with a non-sheared viscosity between 0.5 Pa·s and 200 Pa·s.

Another aspect of the present disclosure includes a method of occluding a vessel of a mammal. The method comprises injecting a bioadhesive into a vessel of a mammal which crosslinks in the vessel to occlude the vessel, wherein the bioadhesive comprises: (i) a biopolymer having one or more first chemically reactive amine groups; (ii) a biocompatible crosslinker having at least two second chemically reactive groups that can chemically react with the one or more first chemically reactive amine groups of the biopolymer; and (iii) a biocompatible rheological modifier.

Embodiments include one or more of the following features individually or combined. For example, the biocompatible rheological modifier can have a viscosity sufficient to displace fluid within the vessel while the biopolymer and biocompatible crosslinker crosslink. In some embodiments, the biocompatible rheological modifier is a shear thinning fluid with a non-sheared viscosity between 0.5 Pa·s and 200 Pa·s. Additional embodiments include injecting the bioadhesive into the vessel by a syringe. In various embodiments, the bioadhesive can be prepared by combining the biopolymer, the biocompatible crosslinker and the biocompatible rheological modifier prior to injecting the bioadhesive into the vessel. The bioadhesive can further comprise a buffer, for example. In some embodiments, the bioadhesive has a gelation time of between 0.5 minute and 40 minutes. Additional embodiments include injecting the bioadhesive into a blood vessel of a mammal having a diameter of between 0.3 mm to 6 mm, or injecting the bioadhesive into a blood vessel of a mammal having a diameter of greater than 6 mm. In still further embodiments, the rheological modifier displaces blood and prevents blood flow back into the blood vessel while the biopolymer crosslinks with the biocompatible crosslinker. Advantageously, the rheological modifier is absorbed into tissue surrounding the blood vessel after the bioadhesive has crosslinked. In various embodiments, the vessel is absorbed into surrounding tissue in a 4 to 8 week period after injection of the bioadhesive into the vessel. In still further embodiments, the biopolymer is an albumin or a chitosan. In some embodiments, the biocompatible crosslinker is a multi-arm PEG having at least two or more N-hydroxysuccinimide (NHS) ester groups as the second chemically reactive groups. In some embodiments, the biocompatible rheological modifier is hyaluronic acid or a salt thereof such as sodium hyaluronate. In still further embodiments, the biopolymer is albumin having one or more primary amines as the first chemically reactive amine groups, the biocompatible crosslinker is a multi-arm PEG having at least two or more N-hydroxysuccinimide ester groups as the second chemically reactive groups, and the biocompatible rheological modifier is sodium hyaluronate.

In accordance with the present disclosure, a method of occluding a blood vessel of a mammal includes: preparing a bioadhesive by combining (i) a formulation including a biopolymer having one or more first chemically reactive amine groups and a biocompatible rheological modifier with (ii) a formulation including a biocompatible crosslinker having at least two second chemically reactive groups that can chemically react with the one or more first chemically reactive amine groups; and injecting the bioadhesive into a blood vessel which crosslinks in the blood vessel to occlude the blood vessel.

Embodiments include one or more of the following features individually or combined. For example, the method can include injecting the bioadhesive into a blood vessel having a diameter between 0.3 mm to 6 mm. The bioadhesive can have a gelation time of between 5 minutes and 40 minutes, for example. In some embodiments, the biopolymer is albumin. In some embodiments, the biocompatible rheological modifier is sodium hyaluronate, and the biocompatible crosslinker is a multi-arm PEG having at least two or more N-hydroxysuccinimide ester groups as the second chemically reactive groups. Additional embodiments include preparing the formulation including the biocompatible crosslinker by combining a multi-arm PEG as the biocompatible crosslinker with a buffer. In some embodiments, the buffer has a pH of between 4.5 and 7.4. In some embodiments, the method includes injecting the biocompatible formulation into a blood vessel having a diameter greater than 6 mm.

In accordance with the present disclosure, a method of occluding a blood vessel of a mammal includes: preparing a bioadhesive by combining (i) a formulation including a biopolymer having one or more first chemically reactive amine groups and a biocompatible rheological modifier with (ii) a formulation including a buffer and a biocompatible crosslinker having at least two second chemically reactive groups that can chemically react with the one or more first chemically reactive amine groups; and injecting the bioadhesive into a blood vessel which crosslinks in the blood vessel to occlude the blood vessel.

Embodiments include one or more of the following features individually or combined. For example, the biocompatible rheological modifier can be a shear thinning fluid with a non-sheared viscosity between 0.5 Pa·s and 200 Pa·s. The method can include injecting the biocompatible formulation into a blood vessel having a diameter of between 0.3 mm to 6 mm, for example. In some embodiments, the bioadhesive has a gelation time of between 5 minutes and 40 minutes. In some embodiments, the buffer has a pH between 4.5 and 7.4. In still further embodiments, the rheological modifier is absorbed into tissue surrounding the blood vessel after the bioadhesive has crosslinked. Additional embodiments include wherein the injected bioadhesive displaces blood in the blood vessel and prevents blood flow back into the blood vessel while the biopolymer and biocompatible crosslinker crosslink in the blood vessel.

Another aspect of the present disclosure includes a kit comprising: (i) a first container including a biopolymer having one or more first chemically reactive amine groups; (ii) a second container including a biocompatible crosslinker having at least two second chemically reactive groups that can chemically react with the one or more first chemically reactive amine groups of the biopolymer; and (iii) a biocompatible rheological modifier included either in the first container or the second container or in a third container.

Embodiments include one or more of the following features individually or combined. For example, the biopolymer can be a protein or a polysaccharide having one or more primary amines as the first chemically reactive amine groups. In other embodiments, the biopolymer is albumin. In still further embodiments, the biopolymer is collagen. The biopolymer can further be a chitosan having one or more first chemically reactive amine groups in some embodiments or a synthetic polymer selected from the group consisting of amine functionalized polyethylene glycols, polyallylamine, and branched polyethylenimine in other embodiments. In some embodiments, the biocompatible crosslinker is a multi-arm PEG having at least two or more N-hydroxysuccinimide (NHS) ester groups as the second chemically reactive groups. In various embodiments, the biocompatible rheological modifier is a shear thinning fluid with a non-sheared viscosity between 0.5 Pa·s and 200 Pa·s. In some embodiments, the biocompatible rheological modifier is hyaluronic acid or a salt thereof such as sodium hyaluronate. In further embodiments, the biopolymer is albumin having one or more primary amines as the first chemically reactive amine groups, the biocompatible crosslinker is a multi-arm PEG having at least two or more N-hydroxysuccinimide ester groups as the second chemically reactive groups, and the biocompatible rheological modifier is sodium hyaluronate. In some embodiments, the biopolymer and the biocompatible rheological modifier are included as a formulation in the first container. In some embodiments, the biocompatible crosslinker is contained in the second container as a formulation having a pH between 4.5 and 7.4. Additional embodiments include, wherein when the contents of the first container, the second container and the biocompatible rheological modifier of the kit are combined to form a formulation, the concentration of the biopolymer in the formulation is 15 wt % or less.

In accordance with the present disclosure, a kit can include: (i) a first container including a biopolymer having one or more first chemically reactive amine groups; (ii) a second container including a biocompatible crosslinker having at least two second chemically reactive groups that can chemically react with the one or more first chemically reactive amine groups of the biopolymer; (iii) a third container including a buffer solution; and (iv) a biocompatible rheological modifier included in any one of the first, second or third containers or in a fourth container.

Embodiments include one or more of the following features individually or combined. For example, the biocompatible crosslinker can be a multi-arm polyethylene glycol having at least two or more N-hydroxysuccinimide (NHS) ester groups as the second chemically reactive groups; and the buffer solution includes citric acid and sodium phosphate dibasic in water for injection (WFI) grade water and has a pH of between 4.5 and 7.4. Other embodiments include wherein the biopolymer is an albumin, and the first container includes sodium hyaluronate as the biocompatible rheological modifier formulated in a buffer solution at a concentration of less than 2%. Additional embodiments include wherein when the contents of the first container, the second container, the third container and the biocompatible rheological modifier of the kit are combined to form a formulation, the concentration of the biopolymer in the formulation is between 5% and 7.5% by weight.

In accordance with the present disclosure, a kit can include: (i) a first container including albumin having one or more first chemically reactive amine groups; (ii) a second container including a multi-arm polyethylene glycol having at least two second chemically reactive groups that can chemically react with the one or more first chemically reactive amine groups of the albumin; (iii) a hyaluronate salt rheological modifier included either in the first container or the second container or in a third container.

Embodiments include one or more of the following features individually or combined. For example, the kit can include a first syringe as the first container. The first syringe can include the albumin and hyaluronate salt rheological modifier as a formulation, and the second container can be a second syringe including the multi-arm polyethylene glycol as a formulation having a pH of between 4.5 and 7.4. Additional embodiments include wherein the multi-arm polyethylene glycol formulation includes citric acid, dibasic phosphate solution and WFI grade water.

Additional advantages of the present invention will become readily apparent to those skilled in this art from the following detailed description, wherein only the preferred embodiment of the invention is shown and described, simply by way of illustration of the best mode contemplated of carrying out the invention. As will be realized, the invention is capable of other and different embodiments, and its several details are capable of modifications in various respects, all without departing from the invention. Accordingly, the drawings and description are to be regarded as illustrative in nature, and not as restrictive.

BRIEF DESCRIPTION OF THE DRAWINGS

Reference is made to the attached drawings, wherein elements having the same reference numeral designations represent similar elements throughout and wherein.

DETAILED DESCRIPTION OF THE DISCLOSURE

The present disclosure relates to bioadhesives and crosslinked gels therefrom. The bioadhesives can be inserted into a vessel of a mammal, e.g., a human, for occluding the vessel. The present disclosure also describes kits that comprise the various components for preparing and applying the bioadhesives. The bioadhesive of the present disclosure include: (i) a biopolymer having one or more first chemically reactive amine groups; (ii) a biocompatible crosslinker having at least two second chemically reactive groups that can chemically react with the one or more first chemically reactive amine groups of the biopolymer; and (iii) a biocompatible rheological modifier.

The biopolymer can be in a formulation, e.g., an aqueous formulation, alone or with other additives such as preservatives and/or pH modifiers. Also, the biocompatible crosslinker can be in a formulation, e.g., an aqueous formulation, either alone or with other additives such as preservatives and/or pH modifiers in the formulation. The biocompatible rheological modifier can also be in a separate formulation, e.g., an aqueous formulation, alone or with other additives such as preservatives and/or pH modifiers. Alternatively, the biocompatible rheological modifier can be included in the formulation with either or both of the biopolymer formulation and/or the crosslinker formulation.

The rheological modifier is provided in the formulation to increase the viscosity of the formulation. The increased viscosity of the formulation is advantageous when inserting the bioadhesive into a blood vessel since the biocompatible rheological modifier facilitates displacement of blood in the vessel and prevents blood flow back into the vessel while the biopolymer and crosslinker form a crosslinked network and adheres to the vessel. Similarly, in other vessels, such as the vas deferens or fallopian tube in a sterilization procedure, the rheological modifier facilitates displacing any fluid that may be present to dilute or wash away the bioadhesive while the bioadhesive crosslinks. While increasing viscosity, the rheological modifier also has shear thinning properties to enable injection of the bioadhesive through a thin gauge needle or catheter.

In one aspect of the present disclosure, the bioadhesive can be used in the treatment of superficial or spider blood vessels. The formulations can also be broadly used to treat larger blood vessels (perforators, varicose veins, arteries), vascular malformations (aneurysms, AVMs, fistula sealant, etc.), and for wound closure applications.

Figure 3:
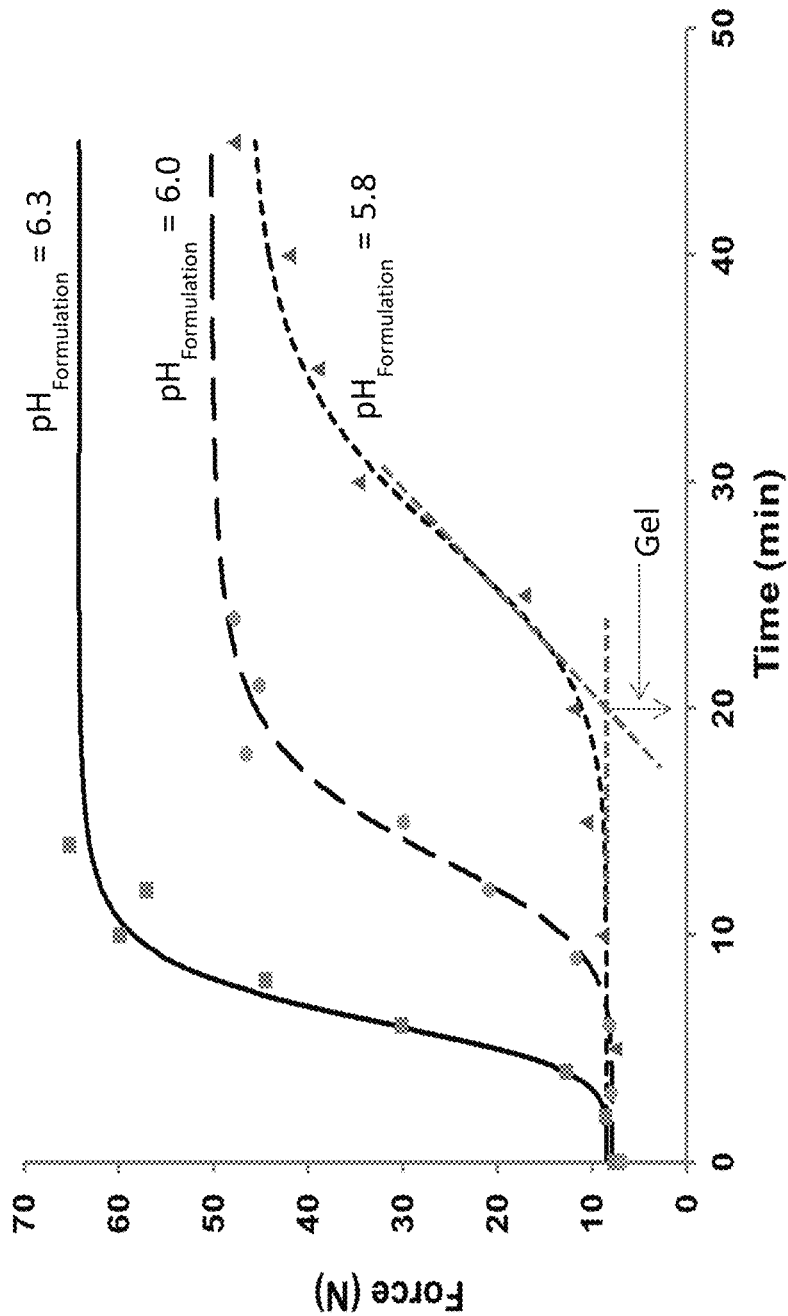
FIG. 3 is a chart plotting force versus time and showing the effect of pH on gelation time for bioadhesives of the present disclosure.

Another aspect of the bioadhesives of the present disclosure is that the formulation can be prepared to gel over a period that is appropriate for specific procedures, such as procedures to occlude a vessel. As used herein, gelation time is defined as the time when a formulation beings to transform from a sol to a gel. With respect to a bioadhesive, the gelation time is the time period from when all the reactive components of the bioadhesive are combined to form a sol which transforms to a gel. The gelation time can be quantified as follows. A bioadhesive is mixed in a large syringe and transferred to several 1 mL syringes, and then extruded through a 30 G needle at a fixed flow rate (1.5 mL/min). The force needed to extrude the bioadhesive is quantified for one of the premixed syringes at various time points and plotted. The data is fitted to a sigmoidal curve and gelation occurs as the fitted lines transition to concave up. Gelation is estimated by the intersection of the tangents to the points immediately before and after the transition. For example, FIG. 3 illustrates the gelation time for three bioadhesives. The formulations were mixed in ten 1 mL syringes for each bioadhesive, extruded through a 30 G needle at a fixed flow rate of 1.5 mL/min, and the force was measured over time (i.e., one syringe was measured at each specific time point, and each data point represents one syringe). The data was fitted to sigmoidal curves for each formulation. As can be seen in FIG. 3, the bioadhesive having a pH of 5.8 had a gel time of approximately 20 minutes. The method described herein for determining the gelation time of a bioadhesive is broadly applicable for other formulations.

Advantageously, bioadhesives of the present disclosure have a gelation time that is sufficient for allowing the preparation of the formulation and use of the formulation in occluding a vessel. Sufficient times will vary depending on a number of factors such as the type of vessel contemplated for occlusion and the particular indication for the bioadhesive. In one aspect of the present disclosure, the gelation time of the bioadhesive is between about 0.5 minute and about 40 minutes, e.g., between about 5 min and about 30 minutes. In other aspects of the present disclosure, the gelation time is more than about 5 minutes. Gelation time is measured from the time when mixing is complete, which takes about 10 seconds.

The gelation time of the bioadhesives of the present disclosure depend on several factors, including: the composition of the formulation, the concentration of the components of the formulation, and the pH of the formulation. While several factors influence gelation time, the pH of the formulation is intended to be the principal factor that affects gelation time for application in small blood vessels. For example, bioadhesives that are more acidic tend to have greater gelation time since the crosslinking reaction between the chemically reactive amine of the biopolymer and second chemically reactive groups of crosslinker tend to take longer in acidic media. Hence, the gelation time of the bioadhesive can be adjusted by adjusting the pH of the formulation. In one aspect of the present disclosure, the pH of the bioadhesives of the present disclosure is less than 7.4, e.g., the pH of the formulations are between about 6.5 and about 5.0 such as between about 6.5 and 5.5. The pH of the formulation can readily be adjusted by adjusting the pH of any of the components used to prepare the formulation such as adjusting the pH of a formulation including the biopolymer or adjusting the pH of a formulation including the crosslinker or by adding a separate buffer with a particular pH to the formulation.

The concentration of the components of the bioadhesive can be varied. In certain embodiments of the present disclosure, the concentration of the biopolymer in the bioadhesive is less than 15% by weight of the total contents of the formulation (wt %), e.g., the concentration of the biopolymer in the bioadhesive is between 7.5 wt % to 5 wt %. The concentration of the biocompatible crosslinker can be between 2 wt % to 5 wt % of the bioadhesive, e.g. from between 3 wt % to 4 wt %, and the concentration of the biocompatible rheological modifier can be between 0.3 wt % to 1 wt % of the bioadhesive, e.g. from between 0.6 wt % to 0.9 wt %.

The bioadhesive can be prepared by combining: (i) a biopolymer having one or more first chemically reactive amine groups; (ii) a biocompatible crosslinker having at least two second chemically reactive groups that can chemically react with the one or more first chemically reactive amine groups of the biopolymer; and (iii) a biocompatible rheological modifier. The biopolymer can be in separate formulations, e.g., in separate aqueous formulations, which can optionally further include other additives such as preservatives and/or pH modifiers. The biocompatible rheological modifier can be in a separate formulation, e.g., an aqueous formulation, alone or with other additives such as preservatives and/or pH modifiers or the biocompatible rheological modifier can be included in either the biopolymer formulation or the crosslinker formulation, or in both.

In an embodiment of the present disclosure, the biopolymer and the biocompatible rheological modifier can be combined as a single formulation and the bioadhesive can be prepared by combining the biopolymer/rheological modifier formulation with a formulation including the crosslinker. The crosslinker formulation can also include a buffer, such as citric acid and disodium hydrogen phosphate (also referred to as sodium phosphate dibasic or dibasic phosphate), in bacteriostatic water, sterile water, or water for injection (WFI). For example, a bioadhesive of the present disclosure can be prepared by mixing the biopolymer and the biocompatible rheological modifier in a first container; mixing the biocompatible crosslinker in a buffer solution in a second container; and mixing the contents of the first container and the second container together to form the bioadhesive.

In certain embodiments, the crosslinker/buffer formulation can be adjusted to have a pH such that the overall pH of the formulation is less than 7.4 when the crosslinker/buffer formulation is combined with the other components of the bioadhesive. For example, e.g. the crosslinker/buffer formulation can have a pH of between 7.4 and 4.5, e.g., a pH between 6.5 and 5.0 such as a pH of between 6.5 and 5.5. By adjusting the pH of the crosslinker/buffer formulation, the gelation time of the formulation can be adjusted.

Figure 1:
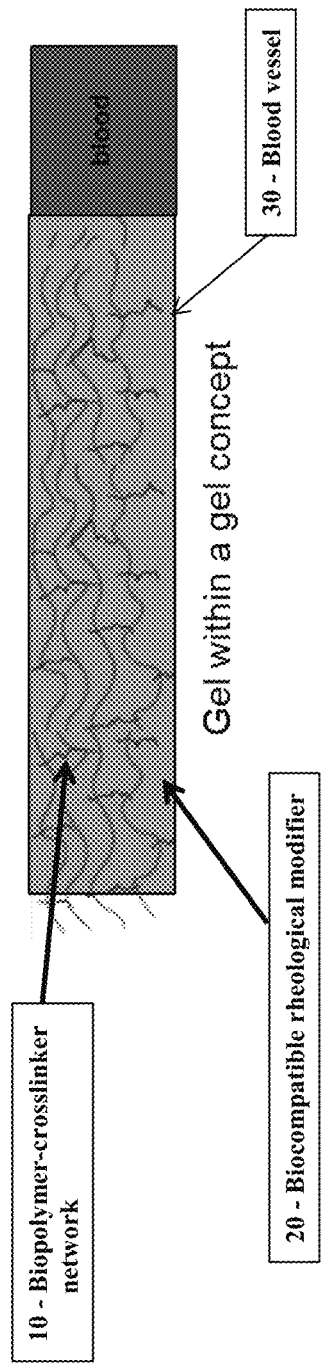
FIG. 1 is schematic illustration of a bioadhesive gel of the present disclosure within a blood vessel.

When the biopolymer, biocompatible crosslinker and biocompatible rheological modifier of the present disclosure are combined, the amine groups of the biopolymer chemically react with the reactive groups of the crosslinker over a period of time to form a crosslinked polymeric network to form the bioadhesive gel that includes the rheological modifier. FIG. 1 schematically illustrates the structure of forming a bioadhesive gel from a bioadhesive of the present disclosure after the formulation had been inserted, e.g., injected, into a blood vessel. As illustrated in FIG. 1, the biopolymer and crosslinker chemically react to form biopolymer-crosslinker polymeric network 10. The biopolymer-crosslinker polymeric network 10 can also be attached to the surrounding wall of the vessel through the reactive groups of the crosslinker. The biocompatible rheological modifier 20 is also included with the bioadhesive, and within the bioadhesive gel for a time after gelation, in the blood vessel 30. The biocompatible rheological modifier has a viscosity sufficient to facilitate the displacement of blood in a blood vessel and substantially prevents blood flow back into the vessel for a time sufficient for the biopolymer and crosslinker to form a crosslinked network within the vessel to form a bioadhesive gel which can eventually be absorbed into surrounding tissue. However, the biocompatible rheological modifier also has shear thinning properties to enable the bioadhesive to be injected through a thin gauge needle, such as a 30 gauge needle.

Biopolymers of the present disclosure include those having one or more first chemically reactive amine groups. Preferably the biopolymer has multiple chemically reactive amine groups such as multiple primary amine groups that can chemically react with the crosslinker. Such biopolymers include proteins and polysaccharide having one or more first chemically reactive amine groups, for example, proteins and polysaccharides having multiple primary amine groups. Proteins useful as biopolymers include, for example, albumin and collagen having one or more first chemically reactive groups. Polysaccharides useful as biopolymers of the present disclosure include chitosans having one or more first chemically reactive groups, e.g., chitosans having multiple primary amines as the first chemically reactive amine groups. Other biopolymers useful for the present disclosure include polyaminoacids having one or more first chemically reactive amine groups such as polylysine, etc. The biopolymers of the present disclosure are not restricted to polymers that are naturally available but can also include synthetic polymers such as amine functionalized polyethylene glycols, polyallylamine and branched polyethylenimine, for example. In certain embodiments, some combinations of these or other biopolymers may also be used.

Biocompatible crosslinkers of the present disclosure include those having at least two second chemically reactive groups that can chemically react with the one or more first chemically reactive amine groups of the biopolymer. Preferably the biocompatible crosslinker has at least three, four, five, six, seven, eight or more second chemically reactive groups that can chemically react with the one or more first chemically reactive amine groups of the biopolymer. In one aspect of the present disclosure, the biocompatible crosslinker is a polyethylene glycol having chemically reactive N-hydroxysuccinimide (NETS) groups which can chemically react with the amines of the biopolymer.

In one aspect of the present disclosure, the biocompatible crosslinker is a multi-arm polyethylene glycol (PEG) having at least two N-hydroxysuccinimide (NETS) ester groups as the second chemically reactive groups. Such crosslinkers include, for example, 4-arm and 8-arm N-hydroxy substituted succinimidyl-PEG (NHS:PEG) crosslinkers.

Biocompatible rheological modifiers of the present disclosure include those that can increase the viscosity of the bioadhesive. Preferably, the rheological modifier exhibits shear thinning effects; that is, the viscosity of the bioadhesive including the rheological modifier has a lower viscosity when a shear force is applied to the formulation. Such a force can occur when the bioadhesive is ejected from a syringe or similar device for inserting the bioadhesive into a vessel.

In one aspect of the present disclosure, the rheological modifier facilitates the displacement of blood in a blood vessel for a time sufficient for the biopolymer and crosslinker to form a crosslinked network without being washed away or diluted. Preferably, the biocompatible rheological modifier does not substantially react with the biopolymer or the biocompatible crosslinker. Rather, the biopolymer and the crosslinker react with each other within the rheological modifier as a gel within a gel.

Useful rheological modifies of the present disclosure include any one or more of polysaccharides, alginates, celluloses (including carboxymethyl, hydroxypropylmethyl, and microcrystalline cellulose), gums (such as xanthan gum and guar gum), dextrans, and biocompatible derivatives and biocompatible salts thereof, as well as some combinations thereof. The biocompatible rheological modifiers are distinct from the biopolymers in that the biocompatible rheological modifiers do not contain any appreciable number of chemically reactive amines and are chosen such that the biocompatible rheological modifier does not substantially react with the biopolymer or the biocompatible crosslinker.

Preferably the rheological modifier is a biocompatible polysaccharide such as hyaluronic acid or a salt thereof, e.g., sodium hyaluronate. Hyaluronic acid, also known as hyaluronan and HA, is a naturally occurring, water soluble polysaccharide, specifically a glycosaminoglycan, which is a major component of the extra-cellular matrix and is widely distributed in animal tissues. HA and salts thereof have excellent biocompatibility and can be readily absorbed into the body when implanted into a mammal. In addition, HA and salts thereof can increase the viscosity of the bioadhesive and assist in displacing blood when injected into a blood vessel, while having shear thinning properties when injected through a needle.

In practicing certain embodiments, the rheological modifier should have or causes a non-sheared viscosity sufficient to displace blood and keep the blood from pushing back into a treatment area while the biopolymer and crosslinker crosslink. Blood has a viscosity around 3 cp (0.003 Pa·s). Glycerin, which is a chemical sometimes used within blood vessels, has a viscosity around 10 cp (0.01 Pa·s) when in a 72% w/v glycerin/water solution. However, that viscosity allows blood to bleed back into the treatment area quickly, which would not allow enough time for a biopolymer and crosslinker to crosslink. Thus, a rheological modifier with greater viscosity should be used to enable enough time for the biopolymer and crosslinker to crosslink, while preferably exhibiting shear thinning properties to enable the bioadhesive to be injected through a thin gauge needle. For example, the biocompatible rheological modifier may be a shear thinning fluid with a non-sheared viscosity between 500 cp (0.5 Pa·s) and 200,000 cp (200 Pa·s), e.g., between 10,000 cp (10 Pa·s) to 200,000 cp (200 Pa·s). One such rheological modifier can include hyaluronic acid or salt thereof as an aqueous solution. Hyaluronic acid or salt thereof may be prepared in an aqueous 1% w/v concentration which will have a non-shear viscosity around 100,000 cp (100 Pa·s) depending on the molecular weight of the hyaluronic acid used.

In practicing certain embodiments of the present disclosure, the bioadhesive can be inserted, such as by injection through a needle, into a vessel, such as a blood vessel, to occlude the vessel. The bioadhesive of the present disclosure includes: (i) a biopolymer having one or more first chemically reactive amine groups; (ii) a biocompatible crosslinker having at least two second chemically reactive groups that can chemically react with the one or more first chemically reactive amine groups of the biopolymer; and (iii) a biocompatible rheological modifier. As the bioadhesive is injected into the blood vessel, the bioadhesive displaces the blood. After the bioadhesive is insertion into the vessel, the rheological modifier prevents blood from flowing back into the treated area while the biopolymer crosslinks with the biocompatible crosslinker to form a bioadhesive gel, and the crosslinked networked can attach to the vessel walls through reactions with the biopolymer and/or crosslinker, thereby forming an occlusion in the vessel. Once crosslinked, the bioadhesive gel may have a color that cannot be seen through the skin, and may have a tactile feel similar to the vessel into which the bioadhesive was injected. Over time, the biocompatible rheological modifier will be absorbed into the surrounding tissue, as will the bioadhesive gel occlusion and the vessel.

In certain embodiments, the bioadhesive can be prepared by combining (i) a formulation including a biopolymer having one or more first chemically reactive amine groups and a biocompatible rheological modifier with (ii) a formulation including a biocompatible crosslinker having at least two second chemically reactive groups that can chemically react with the one or more first chemically reactive amine groups. The formulation including the biocompatible crosslinker can further include a buffer having a pH of between 7.4 and 4.5, e.g., a pH of between 6.5 and 5.2.

As explained above, adjusting the pH of the bioadhesive such as by adjusting the pH of one or more of the component formulations to prepare the bioadhesive, can adjust the gelation time of the formulation. The gelation time of the formulation can be adjusted such that it will crosslink quickly, for example, after about half a minute, or more slowly, such as after about 5 minutes. The gelation time can be adjusted so that the bioadhesive can range from about 1 minute to about 40 minutes, more preferably between about 5 minutes and 40 minutes. When the gelation time is greater than 5 minutes, the bioadhesive is particularly suited for the treatment of superficial or spider blood vessels. The formulations can also be broadly used to treat larger blood vessels (perforators, varicose veins, arteries), vascular malformations (aneurysms, AVMs, fistula sealant, etc.), and, for the faster gelation times, for wound closure applications.

Figure 2:
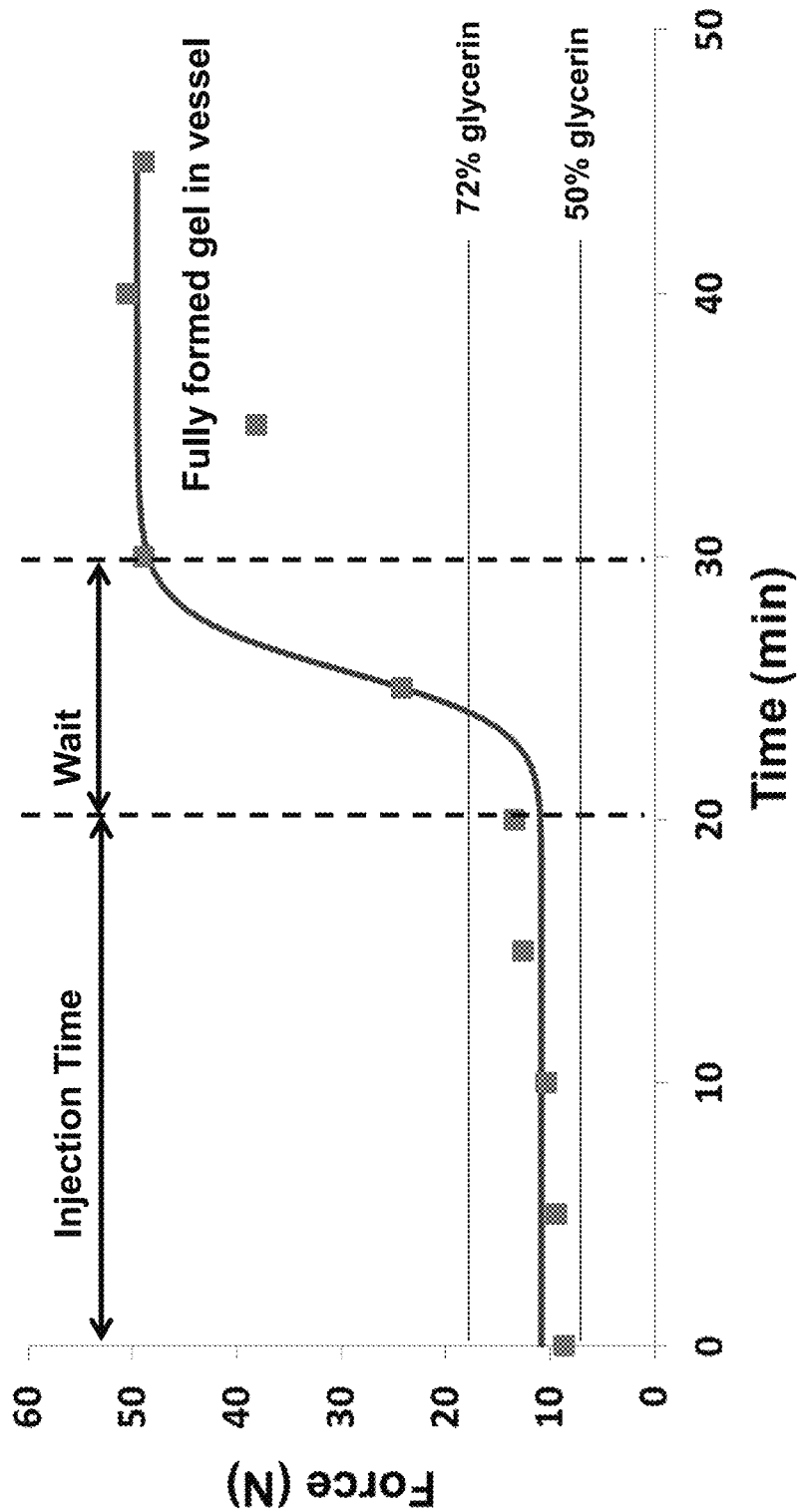
FIG. 2 is a chart plotting the force needed to eject a bioadhesive of the present disclosure at a rate of about 1.5 ml/min from a one (1) ml syringe through a 30 gauge needle versus time and showing the gelation time for the particular formulation.

FIGS. 2 and 3 illustrate properties of a bioadhesive of the present disclosure useful for occluding blood vessels. As shown in FIG. 2, the bioadhesive can be injected into a blood vessel for a period of about 20 to 25 minutes after the components of the bioadhesive are combined and transferred into a syringe. During this injection time period, the force needed to eject the formulation from the syringe is similar to the force needed to eject a 50% (w/v) and 72% (w/v) glycerin/water solution, i.e., between about 7 N and 17 N, through the same size needle. The 50% (w/v) and 72% (w/v) glycerin/water solutions represent the properties of other fluids currently used to treat blood vessels by injection through a needle into the blood vessel. After about 25 minutes, the formulation becomes increasingly more difficult to eject from the syringe due to the formation of the crosslinked polymer.

FIG. 2 further illustrates that during the first 20 minute time period of this bioadhesive embodiment, the formulation can be prepared and then injected into a blood vessel through a needle, such as a 30 gauge needle. During the first 20 minutes, the biocompatible rheological modifier will displace blood, hold the bioadhesive in place, and prevent blood from washing the formulation away. After 20 to 30 minutes, the injected formulation crosslinks in the blood vessel and is more or less fully formed as an occlusion such that the patient can be released from the treatment.

FIG. 3 shows how adjusting the pH of a formulation including the crosslinker prior to combining the crosslinker formulation with a biopolymer and rheological modifier can change the gelation time. As shown in FIG. 3, the gelation time can be adjusted from about 40 minutes to about 5 minutes. Short gelation times are advantageous for applying the bioadhesive of the present disclosure to, for example large blood vessels or fistula sealing.

In an aspect of the present disclosure, a bioadhesive is injected into a blood vessel of a mammal, such as a human, to occlude the blood vessel. The methods of the present disclosure are applicable to injecting the formulation into a blood vessel having a diameter of between 0.3 mm to 6 mm and injecting the formulation into a blood vessel having a diameter of greater than 6 mm. The injected bioadhesive can rapidly and completely occlude the vessel followed by absorption of the treated vessel and the bioadhesive gel occlusion into surrounding tissue over time.

In another aspect of the present disclosure, the components of the bioadhesive can be provided in a kit. For example, the kit can comprise: (i) a first container including a biopolymer having one or more first chemically reactive amine groups; (ii) a second container including a biocompatible crosslinker having at least two second chemically reactive groups that can chemically react with the one or more first chemically reactive amine groups of the biopolymer; and (iii) a biocompatible rheological modifier. The biocompatible rheological modifier can advantageously be included in either the first container or the second container. Alternatively, the biocompatible rheological modifier can be included in a third container such that the kit would comprise three separate containers. The kit can also include another container including a buffer solution. The buffer solution can be used for adjusting the pH of the components of the bioadhesive prior to preparing the formulation or can be added directly to the formulation prepared from the biopolymer, crosslinker and rheological modifier.

The kit can also include instructions on how to combine the various components of the kit to prepare and apply the bioadhesive. The instructions can be included as an insert, incorporated into the container(s) and/or in the packaging of the kit.

In an embodiment of the present disclosure, the kit includes: (i) a first container, e.g., a syringe, including albumin having one or more first chemically reactive amine groups; (ii) a second container including a multi-arm polyethylene glycol having at least two second, e.g., at least three, chemically reactive groups that can chemically react with the one or more first chemically reactive amine groups of the albumin; and (iii) a hyaluronate salt rheological modifier included either in the first container or the second container or in a third container.

EXAMPLES

The following examples are intended to further illustrate certain preferred embodiments of the invention and are not limiting in nature. Those skilled in the art will recognize, or be able to ascertain, using no more than routine experimentation, numerous equivalents to the specific substances and procedures described herein.

Biomaterials: Recombinant Human Albumin was obtained from Invitria (Fort Collins, Colo.) as a 25% stock solution (Albipur DF) or as a powder (Albumin DX LR). Polyethylene Glycol (PEG) crosslinker with a molecular weight of 15 kDa was obtained from Jenkem (Plano, Tex.). Two forms of an 8-arm N-hydroxy substituted succinimidyl-PEG (NHS:PEG) crosslinker were used, which were an 8-arm PEG Succinimidyl Succinate (8ARM-PEG-SS) or an 8-arm PEG Succinimidyl Glutarate (8ARM-PEG-SG). Sodium Hyaluronate (Pharm Grade 150 or Pharm Grade 80) was obtained from FMC Corporation (Novamatrix) (Sandvika, Norway).

Buffers and Preservatives: Citric acid and dibasic sodium phosphate buffer salts were obtained from Sigma Aldrich (St Louis, Mo.). Sterile 1× phosphate buffered saline (PBS) was obtained from Fisher Scientific (Waltham, Mass.). Sodium octanoate and N-acetyl tryptophan preservative compounds were obtained from Sigma Aldrich. Sodium octanoate and N-acetyl tryptophan can be added to a formulation for sterilization and shelf-life extension.

Preparation of Polymer Blends

A sodium hyaluronate solution was prepared by combining 1.5 g of sodium hyaluronate with 100 mL of 1X PBS in a beaker with constant stirring at 600 RPM at 4° C. for an approximate 12 hour period. An albumin solution was prepared by combining 25 g of albumin in a beaker with 100 mL of water for injection (WFI) grade water with constant stirring at 600 RPM at 4° C. over a period of about 12 hours. Sodium hyaluronate/albumin formulations were prepared, for example, by either: (a) adding 60 mL of Albumin solution (25% w/v) to 100 mL of sodium hyaluronate solution (1.5% w/v) with stirring at 300 RPM for 4 h, or (b) adding 33 mL of Albumin solution (25% w/v) to 100 mL of sodium hyaluronate solution (1.5% w/v) with stirring at 300 RPM for 4 h.

Preparation of Citrate-Phosphate Buffers for 8-Arm 15 kDa NHS:PEG

A 0.1M citric acid solution stock in WFI grade water was prepared and a 0.2M Dibasic sodium phosphate solution stock in WFI grade water was also prepared. Buffer solutions were prepared from these stock solutions by mixing the citric acid and dibasic sodium phosphate stock solutions at certain volume ratios to obtain a target pH for the buffer. The pH of the buffer governs the gelation time of the bioadhesive. Table 1 is presented below for the volume ratio and target pH for a bioadhesive including pH of 5.2, 5.8 and 6.5.

TABLE 1

| 0.2M Dibasic sodium phosphate (ml) | 0.1M citric acid (ml) | pH |
|---|---|---|
| 5.4 | 44.6 | 2.6 |
| 7.8 | 42.2 | 2.8 |
| 10.2 | 39.8 | 3.0 |
| 12.3 | 37.7 | 3.2 |
| 14.1 | 35.9 | 3.4 |
| 16.1 | 33.9 | 3.6 |
| 17.7 | 32.3 | 3.8 |
| 19.3 | 30.7 | 4.0 |
| 20.6 | 29.4 | 4.2 |
| 22.2 | 27.8 | 4.4 |
| 23.3 | 26.7 | 4.6 |
| 24.8 | 25.2 | 4.8 |
| 25.7 | 24.3 | 5.0 |
| 26.7 | 23.3 | 5.2 |
| 27.8 | 22.2 | 5.4 |
| 29.0 | 21.0 | 5.6 |
| 30.3 | 19.7 | 5.8 |
| 32.1 | 17.9 | 6.0 |
| 33.1 | 16.9 | 6.2 |
| 34.6 | 15.4 | 6.4 |
| 36.4 | 13.6 | 6.6 |
| 40.9 | 9.1 | 6.8 |
| 43.6 | 6.5 | 7.0 |

A crosslinker buffered solution was prepared by combining 0.15 g of 8-arm NHS:PEG and 1 mL of any of a citric acid and dibasic sodium phosphate buffer solution. The volume ratio of the citric acid and dibasic sodium phosphate will determine the pH of the solution as provided in the table above. It is preferable that the crosslinker buffered solution is prepared immediately prior to use in preparing a bioadhesive gel.

Bioadhesives Including HA

Bioadhesives were prepared by mixing a biopolymer, a biocompatible crosslinker and a biocompatible rheological modifier, as described above. In this example, 4 mL of the polymer blend described above was transferred into a 5 mL syringe. A solution of 1 mL of the NHS:PEG dissolved in a citrate-phosphate buffer was transferred into another 5 mL syringe. The two syringes were then connected to each other by a luer adapter and the contents of the syringes were mixed by moving the contents of the two syringes back and forth for about 10 times to prepare the bioadhesive. The entire 5 mL formulation was then transferred to one of the syringes and the second syringe removed leaving the luer adapter attached to the syringe with the 5 mL of formulation. The bioadhesive was then transferred to 5 syringes of 1 mL each for injections through a 30 gauge needle.

Bioadhesive Gel

Several bioadhesive gels were prepared by combining a first formulation including albumin and sodium hyaluronate with a second formulation including an 8-arm NHS:PEG with citric acid and dibasic sodium phosphate buffers. The various bioadhesive gels were prepared from various cross-linker formulations having a buffer pH range of between 6.5 and 5.2, which was measured as described below.

Control of the Rate of Gelation

The rate of formation of the cross-linked network of albumin and NHS:PEG (i.e., gelation) can be controlled by the pH of the bioadhesive. To increase the rate of cross-linking, the pH of the formulation is increased, and conversely, to decrease the rate of cross-linking, the pH of the formulation is decreased. The pH of the formulation is controlled principally by the addition of a buffer in terms of both the buffer strength and buffer pH.

FIG. 3 shows the effect of pH of the bioadhesive on the rate of gelation of a formulation containing 7.5 wt % human serum albumin, 0.75 wt % sodium hyaluronate and 3 wt % 8ARM-PEG in water for injection at room temperature. The rate of gelation can also be controlled by adjusting the concentration of albumin and the cross-linker. The buffer was included in the solution with the 8ARM-PEG. The gelation time is the amount of time required for the formulation to transform from the liquid state to the cross-linked gel state (as defined above). An advantage of the present disclosure is that the onset of any appreciable crosslinking can be delayed. As shown in FIG. 3, the gelation time can be adjusted from approximately 20 minutes for a bioadhesive having a pH of 5.8 to approximately 10 minutes for a bioadhesive having a pH of 6.0 by changing the pH of the bioadhesive.

Figure 4:
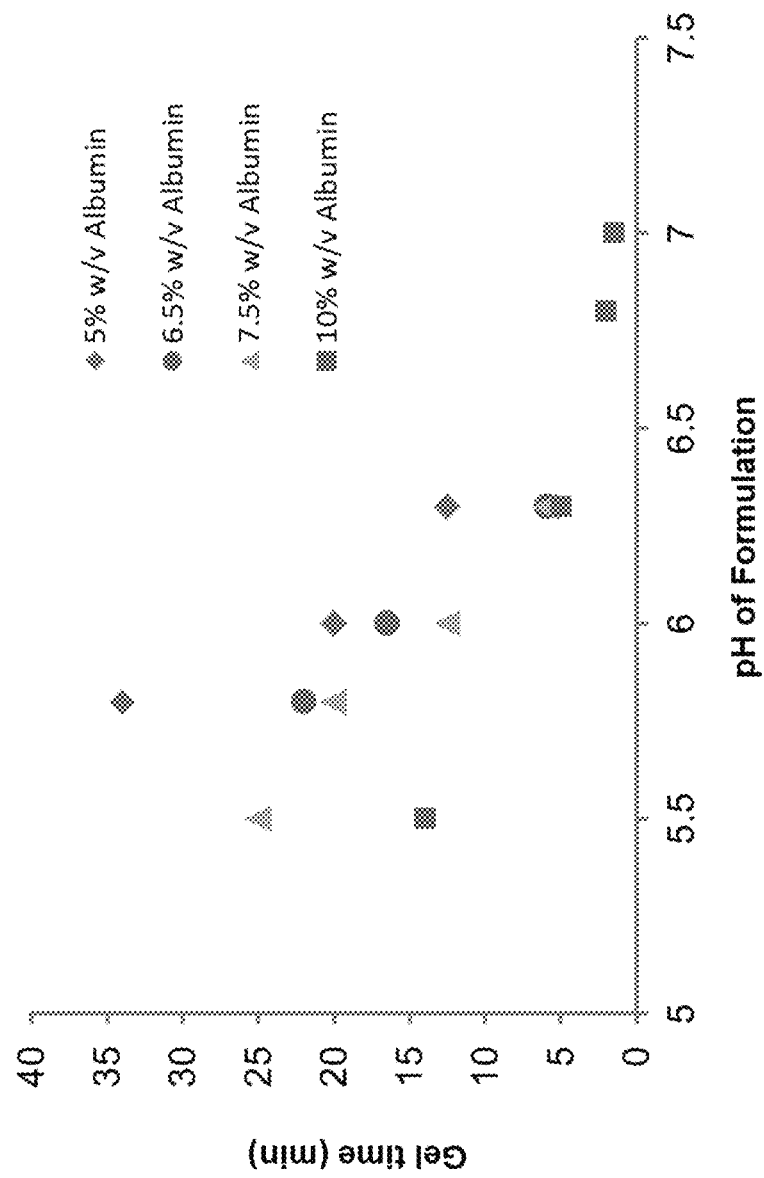
FIG. 4 is a chart showing the effects of pH and biopolymer concentration on gelation time of bioadhesives of the present disclosure.

As also shown in Tables 2 and 3 below, the gelation time can be changed by changing either the pH of the bioadhesive formulation or the concentration of the biopolymer. The data in Tables 2 and 3 below are plotted in FIG. 4, which graphically illustrates the effect of pH and concentration of biopolymer on approximate gelation times. The bioadhesives for Tables 2 and 3 were prepared and measured as follows.

Stock solutions of 25% w/v Recombinant Human Albumin (pH 6.5) and 1.5% w/v Sodium Hyaluronate (pH 6.5) were used to prepare formulations as shown in Table 2 below.

TABLE 2

| Albumin (% w/v) | Sodium Hyaluronate (% w/v) | pH buffer | pH formulation | Gel time (min) |
|---|---|---|---|---|
| 5 | 0.9 | 5.2 | 5.8 | 34 |
| 5 | 0.9 | 5.8 | 6 | 20 |
| 5 | 0.9 | 6.5 | 6.3 | 12 |
| 6.5 | 0.81 | 5.2 | 5.8 | 22 |
| 6.5 | 0.81 | 5.8 | 6 | 16 |
| 6.5 | 0.81 | 6.5 | 6.3 | 6 |
| 7.5 | 0.75 | 5.2 | 5.8 | 20 |
| 7.5 | 0.75 | 5.8 | 6 | 10 |
| 7.5 | 0.75 | 6.5 | 6.3 | 5 |
| 7.5 | 0.75 | 7 | 6.8 | 2 |
| 7.5 | 0.75 | 7.4 | 7 | 1.5 |

Stock solutions of 25% w/v Bovine Serum Albumin (pH 7.0) and 1.5% w/v Sodium Hyaluronate (pH 7.0) were used to prepare formulations as shown in Table 3 below.

TABLE 3

| Albumin (% w/v) | Sodium Hyaluronate (% w/v) | pH buffer | pH formulation | Gel time (min) |
|---|---|---|---|---|
| 10 | 0.6 | 4.6 | 5.5 | 14 |
| 10 | 0.6 | 5.2 | 6 | 8 |
| 10 | 0.6 | 5.8 | 6.3 | 5.5 |
| 10 | 0.6 | 6.5 | 6.8 | 2 |

TABLE 3-continued

| Albumin (% w/v) | Sodium Hyaluronate (% w/v) | pH buffer | pH formulation | Gel time (min) |
|---|---|---|---|---|
| 10 | 0.6 | 7.4 | 7.3 | 0.5 |
| 7.5 | 0.75 | 6.5 | 6.8 | 2.5 |
| 7.5 | 0.75 | 4.6 | 5.5 | 25 |
| 7.5 | 0.75 | 5.2 | 6 | 15 |
| 6.5 | 0.81 | 5.2 | 6 | 17 |
| 6.5 | 0.81 | 5.8 | 6.3 | 6 |
| 5 | 0.9 | 5.8 | 6.3 | 13 |

The pH of the bioadhesives recorded in the tables above was measured with the use of pH test strips having a resolution of 0.5 units. A pH range was identified based on the color of the strips after it was immersed/contacted with the bioadhesive. A mean value (mid-range value) was used to report the pH values in the tables above. Gelation times were approximated by observing the bioadhesive in a syringe every 0.5 min for any distinct change in rheology and/or opacity of the formulation in the syringe and the bioadhesive was considered gelled when a distinct change in rheology and/or opacity of the formulation occurred. It was further observed that this visual method was equivalent to the quantitative method described above of determining gelation time by plotting the force over time of the bioadhesive extruded from a 1 mL syringe through a 30 G needle at a fixed flow rate of 1.5 mL/min and determining the first inflection point of a sigmoidal curve (i.e., where the curve becomes concave up; see FIG. 3) for the formulations tested.

Occluding Blood Vessels

Bioadhesives including HA were injected into a marginal vein of a rabbit to demonstrate rapid and complete vein occlusion followed by controlled absorption of the treated vein into surrounding tissue over a 30-60 day period. Histological findings confirm the presence of collagenous material in the area where the vein originally was with minimal inflammation. Briefly, formulations were injected into the dorsal marginal ear vein of rabbits where the size of veins was in the range of 0.3-2 mm diameter. Injections were performed using a 30 G needle and a 1 mL syringe. Blood pressure in the veins was reduced (to mimic spider vein physiological conditions) by either applying compression distally or by partially occluding the medial artery that supplies blood to the ear. Upon injection, the formulation displaced blood in the vein and gelled over the period of time based on the pH of the formulation and the % w/v of either the biopolymer component or the cross-linker. It may be noted that gel time within a vessel (in-situ) is likely to be faster than measurements reported above as physiological pH is 7.4 and the formulation is in contact with physiological fluid at that pH upon injection.

Bioadhesives Including HPMC

Albumin was sourced and prepared as described above in a 25% stock solution. An 8-ARM NHS:PEG was reconstituted using a citrate-phosphate buffer. A 4% w/v stock solution of hydroxypropylmethyl cellulose (HPMC) from Sigma Aldrich (St. Louis, Mo.) was prepared in phosphate buffered saline (PBS) as a rheological modifier. A 1.5% w/v sodium hyaluronate solution was also prepared as described above. The following bioadhesives were prepared with 3% w/v NHS:PEG, and evaluated as having the specified pH and gelation times:

| Albumin (% w/v) | HPMC (% w/v) | HA (% w/v) | pH formulation | Gel Time (min) |
|---|---|---|---|---|
| 7.5 | 2 | 0 | 6.5 | 5 |
| 7.5 | 1 | 0 | 6.0 | 10 |
| 7.5 | 0.4 | 0.45 | 6.75 | 3 |

Each of these bioadhesives was injectable through a 30 G needle using a 1 mL syringe.

Bioadhesives Including Chitosan

Chitosan Chloride (Protasan UP CL 113) was obtained from Novamatrix (a subsidiary of FMC) (Sandvika, Norway) and prepared as a 4% w/v solution in phosphate buffered saline. An 8-ARM NHS:PEG was reconstituted using a phosphate buffered saline. A 4% w/v stock solution of hydroxypropylmethyl cellulose (HPMC) from Sigma Aldrich (St. Louis, Mo.) was prepared in phosphate buffered saline as a rheological modifier. The following bioadhesives were prepared with 3% w/v NHS:PEG, and evaluated as having the specified pH and gelation times:

| Chitosan (% w/v) | HPMC (% w/v) | pH formulation | Gel Time (min) |
|---|---|---|---|
| 1.2 | 1.0 | 6.0 | 45 |
| 1.6 | 0.8 | 6.5 | 40 |

Each of these bioadhesives was injectable through a 30 G needle using a 1 mL syringe.

Bioadhesives Including Collagen

Porcine Type I collagen was obtained from Sofradim Production (Trevoux, France), and prepared in 0.1M citric acid and adjusted to a pH of 6.5 with 0.2M sodium hydroxide. A 1.5% w/v sodium hyaluronate solution was also prepared as described above. A 4% w/v HPMC solution was prepared as described above. An 8-ARM NHS:PEG was reconstituted using a phosphate buffered saline. The following bioadhesives were prepared with 3% w/v NHS:PEG, and evaluated as having the specified pH and gelation times:

| Collagen (% w/v) | Rheological Modifier (% w/v) | pH formulation | Gel Time (min) |
|---|---|---|---|
| 1.8 | HA - 0.3 | 6.5 | 7 |
| 1.8 | HPMC - 0.4 | 6.5 | 7 |

Each of these bioadhesives was injectable through a 30 G needle using a 1 mL syringe.

Only the preferred embodiments of the present invention and examples of its versatility are shown and described in the present disclosure. It is to be understood that the present invention is capable of use in various other combinations and environments and is capable of changes or modifications within the scope of the inventive concept as expressed herein. Thus, for example, those skilled in the art will recognize, or be able to ascertain, using no more than routine experimentation, numerous equivalents to the specific substances, procedures and arrangements described herein. Such equivalents are considered to be within the scope of this invention, and are covered by the following claims.

What is claimed is:

1. A method of treating a vascular malformation of a mammal, the method comprising:
injecting a bioadhesive into a vascular malformation of a mammal to displace blood in the malformation and prevent blood flow back into the malformation and to crosslink the bioadhesive in the malformation to form an occlusion in the malformation, wherein the bioadhesive comprises: (i) a biopolymer having one or more first chemically reactive amine groups; (ii) a biocompatible crosslinker having at least two second chemically reactive groups that can chemically react with the one or more first chemically reactive amine groups of the biopolymer; and (iii) a biocompatible rheological modifier, and wherein the biopolymer and crosslinker form a crosslinked network and the biocompatible rheological modifier does not substantially react with the biopolymer or the biocompatible crosslinker.

2. The method of claim 1 wherein the biocompatible rheological modifier has a viscosity sufficient to displace fluid within the malformation while the biopolymer and biocompatible crosslinker crosslink.

3. The method of claim 1 comprising injecting the bioadhesive into the malformation by a syringe.

4. The method of claim 1 further comprising preparing the bioadhesive by combining the biopolymer, the biocompatible crosslinker and the biocompatible rheological modifier prior to injecting the bioadhesive into the malformation.

5. The method of claim 1 wherein the bioadhesive has a gelation time of between 0.5 minute and 40 minutes.

6. The method of claim 1, wherein the rheological modifier displaces blood and prevents blood flow back into the blood malformation while the biopolymer crosslinks with the biocompatible crosslinker.

7. The method of claim 1, wherein the rheological modifier is absorbed into tissue surrounding the blood malformation after the bioadhesive has crosslinked.

8. The method of claim 1 wherein the biocompatible rheological modifier is a shear thinning fluid with a non-sheared viscosity between 0.5 Pa·s and 200 Pa·s.

9. The method of claim 1 wherein the biopolymer is an albumin having one or more primary amines as the first chemically reactive amine groups, the biocompatible crosslinker is a multi-arm PEG having at least two or more N-hydroxysuccinimide ester groups as the second chemically reactive groups and the biocompatible rheological modifier is sodium hyaluronate.

10. The method of claim 1 wherein the biopolymer is a protein or a polysaccharide having one or more primary amines as the first chemically reactive groups.

11. The method of claim 1 wherein the biopolymer is albumin.

12. The method of claim 1 wherein the biocompatible cross linker is a multi-arm polyethylene glycol (PEG) having at least two or more N-hydroxysuccinimide (NHS) ester groups as the second chemically reactive groups.

13. The method of claim 1 wherein the biocompatible rheological modifier is hyaluronic acid or a salt thereof.

14. The method of claim 13 wherein the hyaluronic acid or salt thereof has a non-sheared viscosity between 0.5 Pa·s and 200 Pa·s.

15. The method of claim 1 wherein the concentration of the biopolymer in the bioadhesive is less than 15 wt %.

16. The method of claim 1 wherein the bioadhesive has a pH of less than 7.4.

17. The method of claim 1 wherein the biopolymer crosslinks with the biocompatible crosslinker to form a bioadhesive gel.

18. The method of claim 1, wherein the bioadhesive has a gelation time of between 5 minutes and 40 minutes.

19. The method of claim 1 wherein the bioadhesive has a pH of between about 6.5 and about 5.0.

20. The method of claim 1 wherein the occluded malformation is absorbed into surrounding tissue over time after injection of the bioadhesive into the malformation.

21. The method of claim 1 wherein the vascular malformation comprises an aneurysm.

22. The method of claim 1 wherein the vascular malformation comprises an AVM.

23. The method of claim 1 wherein the vascular malformation comprises a fistula.

24. The method of claim 1 wherein the biopolymer comprises chitosan.

25. The method of claim 1 wherein the biocompatible crosslinker comprises genipin.

26. The method of claim 1 wherein the rheological modifier comprises hydroxypropylmethyl cellulose (HPMC).

* * * * *